(12) United States Patent
Palchetti et al.

(10) Patent No.: US 11,691,177 B2
(45) Date of Patent: Jul. 4, 2023

(54) ULTRASOUND PROBE WITH ACOUSTIC AMPLIFIER

(71) Applicant: ESAOTE SpA, Genoa (IT)

(72) Inventors: Paolo Palchetti, Florence (IT); Andrea Grandoni, Vaglia (IT); Iolanda Cuseri, Castiglion Fiorentino (IT)

(73) Assignee: Esaote S.p.A., Genoa (IT)

( * ) Notice: Subject to any disclaimer, the term of this patent is extended or adjusted under 35 U.S.C. 154(b) by 1386 days.

(21) Appl. No.: 15/924,625

(22) Filed: Mar. 19, 2018

(65) Prior Publication Data

US 2018/0290175 A1 Oct. 11, 2018

(30) Foreign Application Priority Data

Apr. 7, 2017 (EP) ..................................... 17165437

(51) Int. Cl.
*B06B 1/06* (2006.01)
*G10K 11/02* (2006.01)
*A61B 8/00* (2006.01)

(52) U.S. Cl.
CPC .......... *B06B 1/0681* (2013.01); *A61B 8/4483* (2013.01); *B06B 1/0677* (2013.01); *B06B 1/0685* (2013.01); *G10K 11/02* (2013.01)

(58) Field of Classification Search
CPC ... B06B 1/0677; B06B 1/0681; B06B 1/0685; A61B 8/4483; G10K 11/02
USPC ....................................................... 310/334
See application file for complete search history.

(56) References Cited

U.S. PATENT DOCUMENTS

| 4,771,205 A | 9/1988 | Mequio |
| 5,664,456 A * | 9/1997 | Eckert ................ G01F 23/2962 |
| | | 310/326 |
| 6,049,159 A | 4/2000 | Barthe |
| 2017/0323133 A1* | 11/2017 | Tsai ......................... B06B 1/06 |

FOREIGN PATENT DOCUMENTS

WO   WO-2005084614 A1 *  9/2005  ............... A61K 8/39

* cited by examiner

*Primary Examiner* — Shawki S Ismail
*Assistant Examiner* — Monica Mata
(74) *Attorney, Agent, or Firm* — Dickinson Wright PLLC

(57) ABSTRACT

A transducer assembly operable to transmit ultrasonic energy in a desired direction towards a zone adapted to be acoustically coupled to an object or area of interest is disclosed which has a transducer layer, a backing material disposed behind the transducer layer with respect to the desired direction, and a back-matching layer disposed between the transducer layer and the backing material to reflect towards the transducer layer part of the ultrasonic energy directed from the transducer layer to the backing material.

The backing layer has an acoustic impedance higher than the acoustic impedance of the back-matching layer. The back-matching material has an impedance less than the impedance of the transducer layer and the transducer layer has a thickness greater than a ¼ of the wavelength of the ultrasound waves the assembly is configured to generate. A process for manufacturing a transducer assembly is also disclosed.

22 Claims, 11 Drawing Sheets

ULTRASOUND PROBE WITH ACOUSTIC AMPLIFIER

FIELD OF THE INVENTION

The disclosure relates to the technical field of ultrasound probes, particularly in the medical field, although it can find applications also in the non-destructive testing field.

STATE OF THE ART

Ultrasound diagnostic technology generally relates to imaging of biological tissue using an ultrasonic transducer probe. The probe includes a transducer which transmits ultrasonic waves and receives ultrasonic echoes reflected from the tissue. The transducer is typically placed on the body surface or internal to a body lumen of a patient in a selected imaging region. The ultrasound transducer generates and directs ultrasonic waves to the imaging region. The transducer then receives ultrasonic waves reflected from the region and converts the received waves into electrical signals that are processed to form a diagnostic image.

Ultrasound transducers typically have several acoustical stacks or layers arranged in one dimension or in two-dimensional (2D) arrays from the furthest (back) to the closest (front) to the area to be placed in contact with the skin and in more in general with the surface of the object to be analysed.

One or more of these layers comprise piezoelectric elements capable of converting a signal into an acoustic wave and vice versa. The remaining layers consist of a backing layer placed between the piezoelectric element and the back of the probe and one or more matching layers located between the piezoelectric elements and the front of the probe.

From U.S. Pat. No. 6,049,159 it is known to use a further layer positioned at the rear-facing part of the piezoelectric elements, i.e. located between the backing layer and the piezoelectric elements. This layer, hereinafter also referred as back-matching layer or dematching layer, is used to reflect upward part of the energy traveling towards the backing to gain sensitivity.

Increase of sensitivity requires a large impedance mismatch between the piezoelectric layer and the back-matching layer to have strong reflection and thus relevant back-propagating energy. This can be achieved both using a material for the back matching layer having an impedance $Z_{layer}$ which is much higher than the impedance $Z_{Piezo}$ of the piezoelectric layer or with a material for the back matching layer having an impedance $Z_{layer}$ which is much lesser than the impedance $Z_{Piezo}$ of the piezoelectric layer following the well-known formula $$\text{Reflection} = \frac{Z_{layer} - Z_{Piezo}}{Z_{layer} + Z_{Piezo}} \quad \text{(eq. 1)}$$

According to the document above, the choice of the impedance of the back-matching layer is critical and has to be carefully done to allow the reflection only of a selected portion of the backwards propagating acoustic energy as bandwidth, sensitivity and pulse duration have contrasting requirements for such an impedance value. It is, however, not an easy task to determine the best value for the impedance of the back-matching layer to take into account of all of these parameters.

In document U.S. Pat. No. 7,621,028, the choice of a high acoustic impedance back-matching layer has been adopted to assure high bandwidth, a key parameter of the performance of a transducer. The materials mentioned in this document are typically a Tungsten material; a Tantalum material; a Tungsten Carbide (WC) material; a WC and Cobalt material; a WC, Cobalt and Tantalum Carbide material; a WC, Nickel and Carbide-Molybdenum oxide (Mo2C) material; and a WC, Nickel, Cobalt and Chromium Carbide (Cr3C2) material all of them having acoustic impedance Z higher than 100 MRayl.

This, however, poses the following drawbacks:

High Z materials are not easy to cut and bind as they normally contain metals. High impedance brings to tight requirements for piezoelectric and de-matching roughness. Furthermore, infra-element cutting is necessary due to their electrical conductivity;

At frequency higher than 5 MHz the quality of the contact surface bonding between piezo and back-matching layer is critical;

The thickness of the piezo material is $\lambda/4$ that represents a problem for high frequency probes.

Thus a need continues to exist to determine an appropriate range of values for the impedance of the back-matching layer, and thus for the choice of materials to be used as back matching layer, to increase the sensitivity of the transducer without significantly affecting the bandwidth and pulse duration.

SUMMARY OF THE INVENTION

It is thus an object of embodiments herein to provide a configuration of a transducer assembly with enhanced sensitivity.

In an embodiment, a transducer assembly operable to transmit ultrasonic energy in a desired direction towards a zone adapted to be acoustically coupled to an object or area of interest comprises:

a) a transducer layer;

b) a backing material disposed behind said transduction material with respect to the desired direction;

c) a back-matching layer disposed between the transducer layer and the backing material to reflect towards said transducer layer part of the ultrasonic energy directed from the transducer layer to the backing material, wherein the back-matching material has an impedance less that the impedance of the transducer layer and the transducer layer has a thickness greater than a ¼, typically ½, of the wavelength of the ultrasound waves the assembly is configured to generate, particularly half of the wavelength.

The inventors found that, if the impedance of the back-matching layer is kept very low, for example less than 5 MRayl, particularly between 0.5 and 4 MRayl, typically between 0.6-2 MRayl, more typically between 0.7 and 1 MRayl, for example by using a polymer such as epoxy, powder/particle filled epoxy, polyurethanes, acrylics or the like, bandwidth and pulse length deterioration can be compensated without caring about the acoustic properties of the back matching layer simply using the components already available in common ultrasound transducers, namely the piezoelectric layer and the front matching layers if the thickness of the piezoelectric layer is increased from $\lambda/4$ up to $\lambda/2$.

To such extent, in an embodiment, the transducer assembly comprises one or more front acoustic matching layers arranged as a stack starting from the transducer layer towards the coupling zone. The front matching layers have a thickness less than half of the wavelength, particularly not greater than 1/3 of the wavelength, and are configured to compensate for increase in pulse duration of the ultrasound wave directed towards the desired direction caused by the low impedance of the back-matching layer.

In this configuration, bandwidth and pulse length can be accommodated by acting on the front matching layers with thickness less than half of the wavelength, particularly not greater than 1/3 of the wavelength, typically in the range 1/4-1/6 of the wavelength. The detailed description will provide some examples of that. The result is an increased sensitivity comparable to high impedance matching layer solutions of the prior art without significantly affecting bandwidth and pulse length requirements.

Increasing the thickness of the piezoelectric layer simplifies the manufacturing process, particularly for high frequency transducers. Furthermore, working with materials having a low acoustic impedance bring additional unexpected advantages.

First of all, materials having adhesive properties like epoxy or powder/particle filled epoxy can be used as back matching layer. In terms of manufacturing steps, that means that piezoelectric bonding can be realized together with back-matching layer fabrication.

If a material having high acoustic impedance (80-100 MRayl and more) is used, the manufacturing process will require a further step of thin film adhesive deposition to coat the back-matching layer.

Secondly, the impedance of the back matching material can be finely controlled adopting air bubble/glass microspheres or thermo-expandable microcapsules particles dispersed in liquid polymers like epoxies, polyurethanes, acrylics.

The microcapsules can, for example, encapsulate liquid low-boiling-point hydrocarbon in shells of thermoplastic resin like $VCl_2$-AN copolymer (chlorine containing shell), AN copolymer (chlorine-free shell). When the microcapsules added to the polymer, for example epoxy, are heated, the shells are softened and expanded with the pressure of gasified hydrocarbon while the polymer cures. A microcapsule expand into 50 to 100 times of its original volume (ballooning) and the cured polymer, where the heated microcapsules are dispersed, can have bulk density as small as 0.4 g/cm$^3$ and acoustic impedance of 0.7-0.8 MRayl. Adjusting microcapsules concentration (% in volume) in polymer and curing schedule acoustic impedance can be fine-tuned.

Impedance lowering can be obtained also adding to the polymer the above microcapsules already expanded prior to use.

By the way, what is here presented should be interpreted to embrace the corresponding materials that have been described and their equivalent but not limited to any material types, which can be adopted for the purpose.

This allows to fine-tune the impedance of the back matching layer as an improvement according to embodiments herein.

According to an aspect, embodiments also relate to a process for manufacturing a transducer assembly operable to transmit ultrasonic energy in a desired direction towards a zone adapted to be acoustically coupled to an object or area of interest, the process comprising:
  providing a transducer layer,
  providing a backing layer;
  providing a back-matching material having acoustic impedance less than the acoustic impedance of the transducer layer, for example comprising one or more polymers, particularly epoxies, polyurethanes, acrylics or the like;
  direct casting the back matching material either on the backing layer to realize a back-matching/backing subassembly or on the transducer layer to realize a transducer/back-matching subassembly;
  bonding either the transducer layer with the back-matching/backing subassembly or the transducer/back-matching subassembly with the backing layer.

The process may further comprise:
  preparing the surface of the transducer layer or of the backing layer for wettability increase and adhesion enhancement of the back-matching material or transducer layer;
  grinding of the back-matching material to a pre-determined thickness.

According to an embodiment, before direct casting the back-matching material on the backing layer or on the transducer layer, a process comprises:
  providing air bubble/glass microspheres or thermo-expandable microcapsules;
  adding the microcapsules to the back-matching material;
  mixing the back-matching material with the thermo-expandable microcapsules.

The process may further comprise curing the back-matching material or the back-matching/backing subassembly or the transducer/back-matching subassembly to control the acoustic impedance of the back-matching material.

The curing step may be performed at a temperature that allows the microcapsules to expand from 50 to 100 times their original volume to bring the density of the back-matching material less than 0.6 g/cm3, typically in the range 0.3-0.5 g/cm3, more typically equal or less than 0.4 g/cm3 and thus the acoustic impedance of the back-matching material less than 1 MRayl, typically between 0.6-0.9 MRayl, more typically between 0.7-0.9 MRayl. The microcapsules may, for example, encapsulate liquid low-boiling-point hydrocarbon in shells of thermoplastic resin like $VCl_2$-AN copolymer or AN copolymer.

Further improvements of the invention will form the subject of the dependent claims.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION OF A PREFERRED EMBODIMENT

Figure 1:
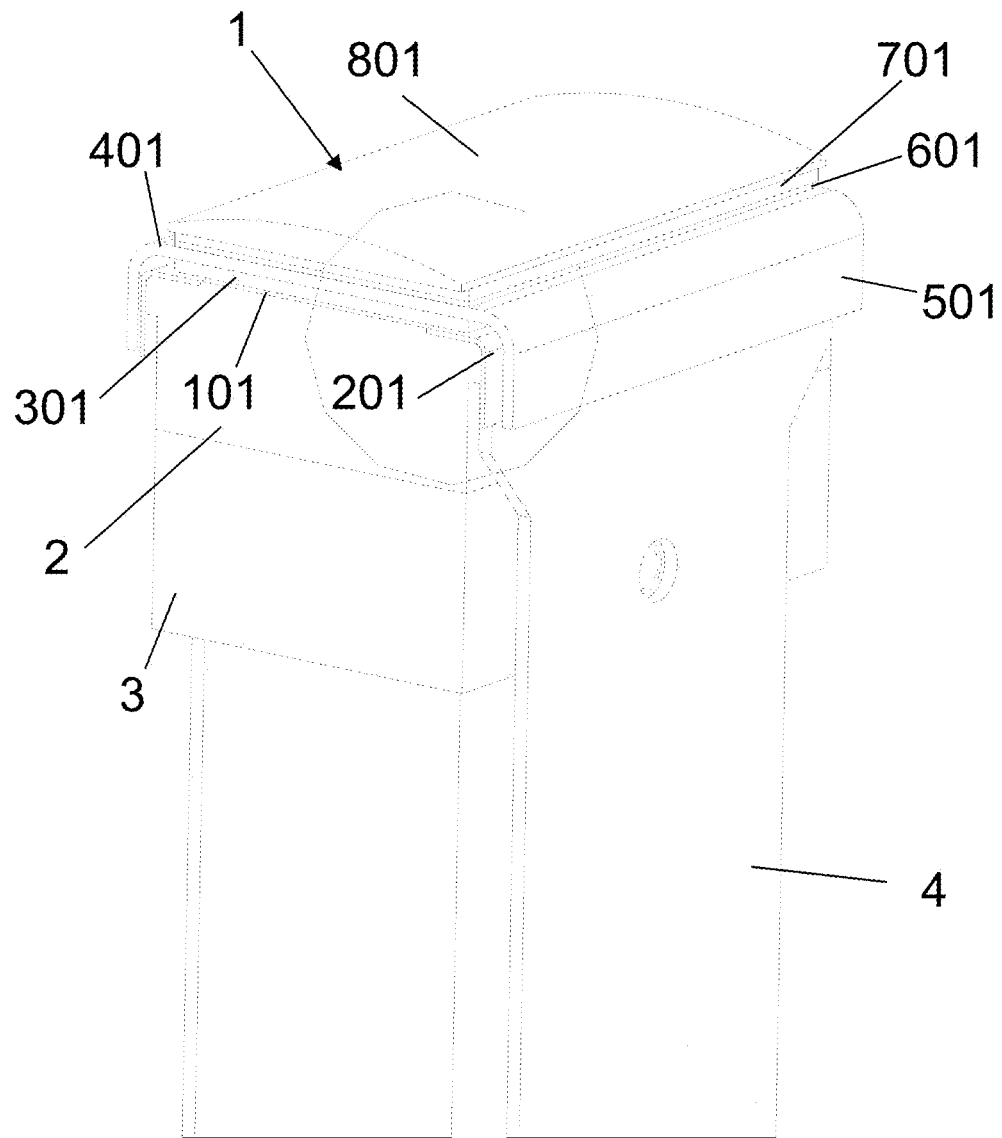
FIG. 1 shows a perspective view of a conventional probe according to the state of the art.
Figure 2:
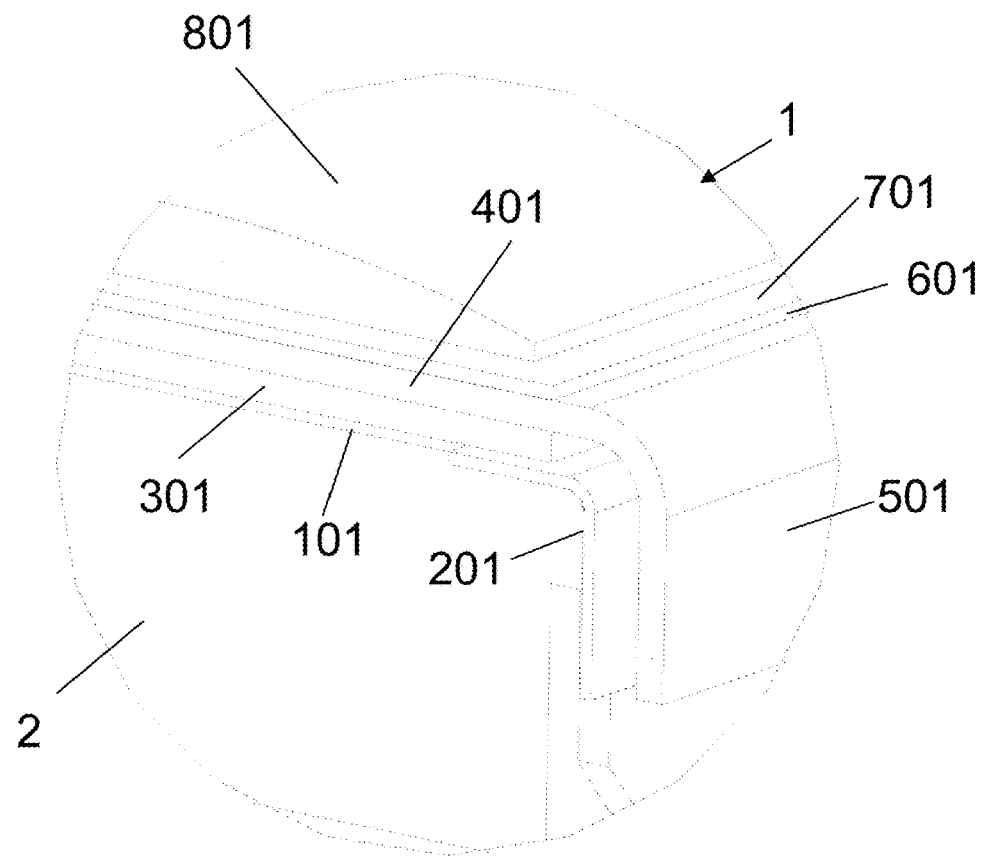
FIG. 2 shows an enlarged view of the head of the probe according to FIG. 1.
Figure 3:
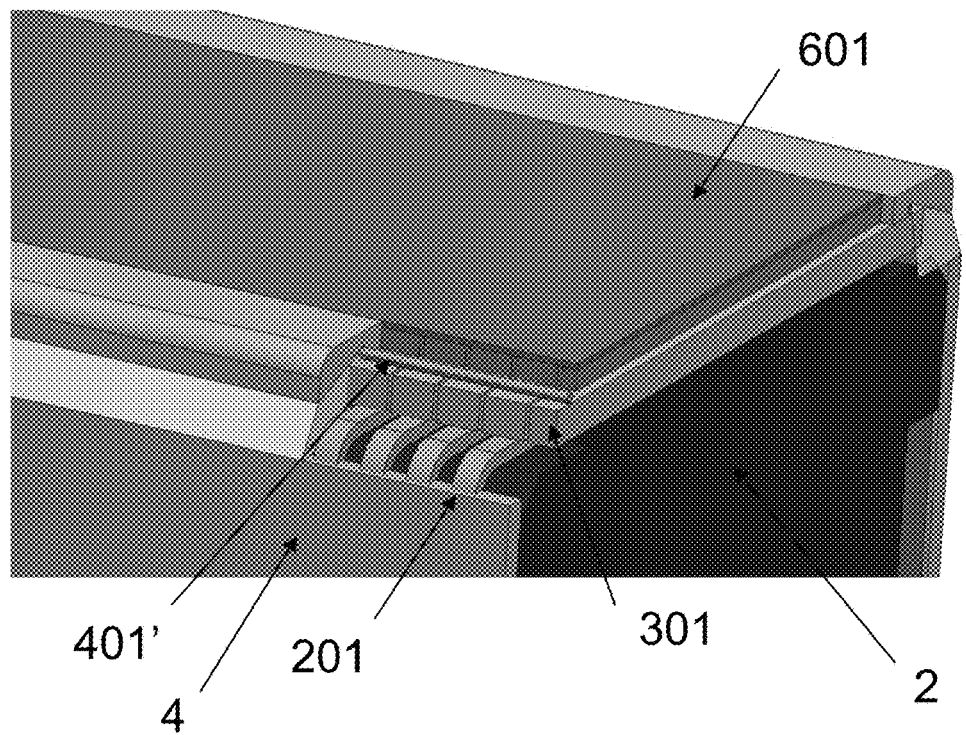
FIG. 3 schematically shows a probe head with ground wire connections arranged to contact transducer elements of a same row.

Referring to FIGS. 1 to 3, a conventional probe is illustrated therein. The probe comprises an ultrasound waves emitting and receiving head 1, which has a front side from which the ultrasound waves are emitted in the direction against a target, such as a body under examination, and on which the reflected ultrasound waves or incoming ultrasound waves impinge and are sensed. The ultrasound head 1 has a back side 3 which is opposite to the said front side and which is oriented towards the inside of a probe casing and towards means for supporting the probe head provided inside the probe casing.

The probe head 1 comprises, in an order starting from the back side of the said head towards the front side of the said head, which order corresponds also to the direction of propagation of the emitted ultrasound waves, a first layer 101 formed by an array of contact electrodes. Each contact electrode of this layer 101 of contact electrodes has a separate electric connection line to a corresponding contact pin on a contact termination provided along at least one edge of the layer of contact electrodes and indicated with 201. The layer 101 of contact electrodes is typically in the form of an array of at least electrically separated contact electrodes since each one of the said contact electrodes has the function of feeding the electric excitation signal to the associated transducer and of collecting the electric receipt signal from the associated transducer when the said transducer is mechanically excited by an impinging ultrasound wave. Some electrodes could be short circuited as in 1.25 D, 1.5 D or 1.75 D probes.

On the layer formed by the array of contact electrodes, an array of piezoelectric elements 301 is laid. Each one of the piezoelectric elements forms an emitting and receiving transducer. Piezoelectric elements are typically fabricated from lead zirconate titanate (PZT), PZT-resin composite or Single Crystal material. The single transducers are each one coincident and in electric contact with one of contact electrodes of the layer 101. In a possible configuration, a further layer of conductive material 401 is laid on the layer 301 formed by the array of transducers. The conductive material of the layer 401 is in electric contact with each one of the said piezoelectric elements and is connected to ground potential by means of a contact termination 501. The layer 401 of conductive material forms the ground electrode of the transducers of the layer 301. The layer 401 may be in the form of an array of ground electrodes, but since the ground potential is common to every of the transducers of the layer 301 there is no need to provide separate ground electrodes for each transducer, so that the said layer 401 can be easily formed by a continuous layer of conductive material. Alternatively, the ground connections may be formed by a microscopic section wire 401' contacting elements belonging to a same raw as shown in FIG. 3. Other ground connection geometries are obviously possible, such as, for example, of the so-called wrap-around type.

On the array of piezoelectric material elements 301 matching layers are provided which are indicated with numerals 601 and 701 in FIGS. 1 and 2. These layers (two in the example of FIG. 2, one in FIG. 3) have the function of adapting the acoustic impedance of the piezoelectric elements to the acoustic impedance of the target. Normally two or three layers are used in order to provide a progressive stepwise adaptation, which also allows to maintain a sufficiently large bandwidth for the passing ultrasound waves. In each material, the acoustic impedance is given by the product of density times speed of sound and can be considered equivalent to the electrical impedance for an electrical circuit with many power transfer stages. The thickness of each matching layer generally follows the $\lambda/4$ rule, so they depend on their operating frequency (generally from 2 MHz to 12 MHz for standard imaging probes) and speed of sound in each material. Matching layer are generally manufactured from epoxy resin loaded with metallic particles. In the configuration with grounded conductive layer 401 (see FIGS. 1 and 2) the first matching layer 601 is generally placed above such grounded layer 401. In case of wiring connection 401' as in FIG. 3, the first matching layer 601 is in direct contact with the piezoelectric elements 301.

Typically, the first matching layer 601 is made of a material having an acoustic impedance of about 5 to 12 MRayl and the last matching layer 701 has an acoustic impedance of about 2 MRayl.

As a last element, on the matching layer 701, an acoustic lens 801, typically of silicone rubber, is placed which forms the interface between the head of the probe 1 and the surface of a target body. The aim of such a lens is to focus the ultrasound beam in the elevation plane.

The contact terminations 201 and 501 of the layer 101 formed by the array of contact electrodes and of the layer 401 or wires 401' formed by the grounded conductive material are electrically and mechanically connected to a printed circuit board 4 which provides the necessary conductive tracks which are connected to a probe connection cable (not shown) via connector 8 and which cable connects the probe with an ultrasound apparatus as for example an ultrasound imaging apparatus.

A multi-element ultrasonic transducer array is generally formed from a block of piezoelectric material, which may be either a ceramic or a polymer. The block is cut or diced into one or more rows of individual elements to form the array. The element-to-element spacing is known as the "pitch" of the array and the spaces between individual elements are known as "kerfs." The kerfs may be filled with some filler material, generally a damping material having low acoustic impedance that blocks and absorbs the transmission of vibrations between adjoining elements, or they may be air-filled. The array of elements may be left in a linear configuration in which all of the elements are in a single plane, or the array may be bent or curved for use as a convex or concave array.

Before the piezoelectric material is diced into individual array elements it is generally coated with metallic electrode material on the top (also referred to as the front, or transmit/receive side) and bottom of the bar. The electrodes on the top of the elements are conventionally connected to an electrical reference potential or ground, and individual conductors are attached to electrode areas on the bottom of the bar to electrically connect to each subsequently formed element. These conductors are then conventionally potted in an acoustic backing material as described, for example, in U.S.

Pat. No. 4,825,115 which fills the space below the transducer elements and between the wires, and damps acoustic vibrations emanating from the bottom of the transducer array. Alternately, the conductors and backing material may be preformed in a block of backing material containing parallel spaced wires, which is then attached to the piezoelectric as described in U.S. Pat. No. 5,329,498 and U.S. Pat. No. 5,267,221. The piezoelectric bar and electrodes are then diced while attached to the backing material. As the bar is diced into individual elements, the metal plating is simultaneously cut into individual electrically separate electrodes for each transducer element. The transducer is completed by bonding front matching layers and the acoustic lens.

The result is a stack of layers starting from the backing 2 to the acoustic lens 801.

The backing material 2 acts both as a support and as a damping device for the back-travelling acoustic wave, to minimize reverberations and ringing. Backing material is generally a special hard rubber compound with poor thermal conductivity. A metallic, typically aluminium, block 3 acts as a support for the backing material 2. Where the term "backing" occurs it is understood as meaning a solid mass, of suitable geometry, on which the piezoelectric elements are mounted; when this component is excited by a voltage pulse, the oscillation is dampened and the reduction in the amplitude between successive oscillations depends on the material with which the component is combined. This base must therefore have particular acoustic properties in terms of impedance and absorption in order to obtain the desired level of attenuation. The impedance of the backing material is typically higher than 4 MRayl, more typically between 6 MRayl and 8 Mrayl.

This mechanism, nevertheless, causes the loss of a substantial part of the energy generated by the piezoelectric active material, because half of it is directed downward, towards the backing, and is lost into it being converted into heat.

Figure 4:
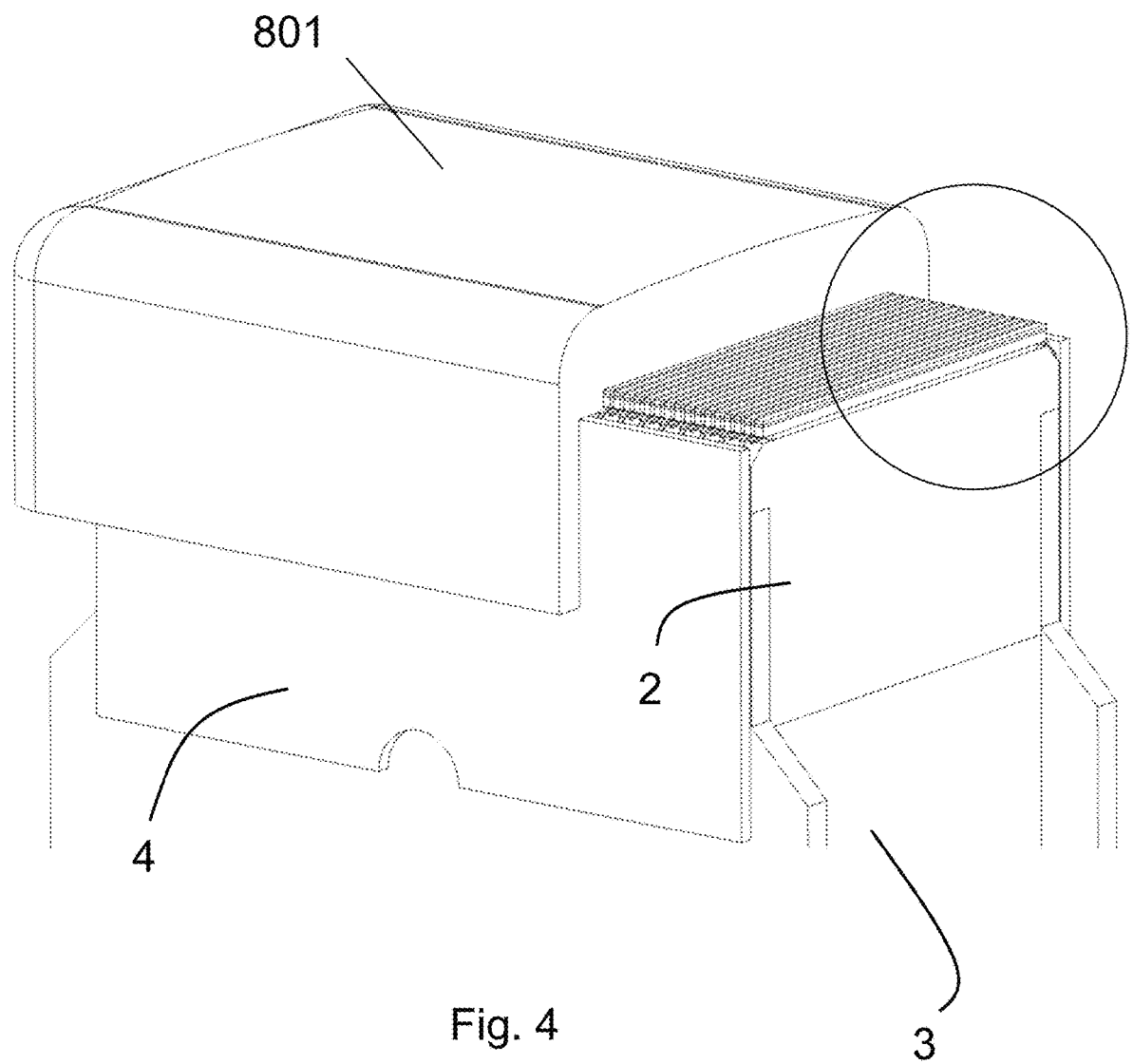
FIG. 4 schematically shows a probe head according to an embodiment.
Figure 5:
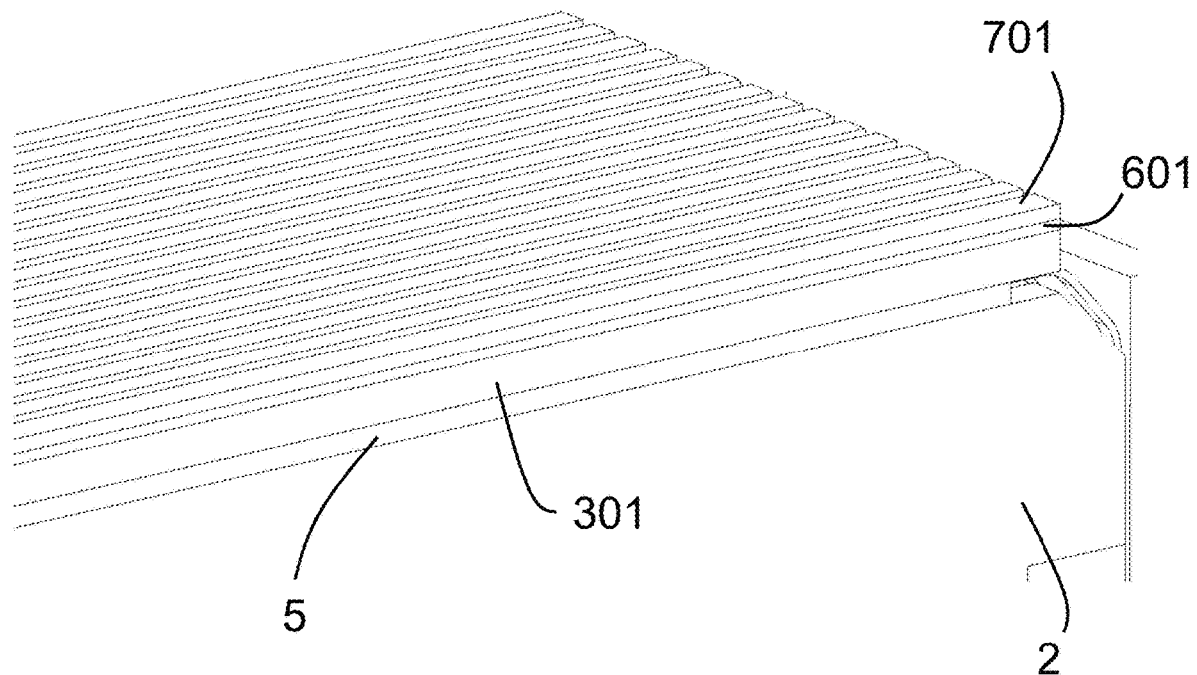
FIG. 5 shows an enlarged view of the head of the probe according to FIG. 4.
Figure 6:
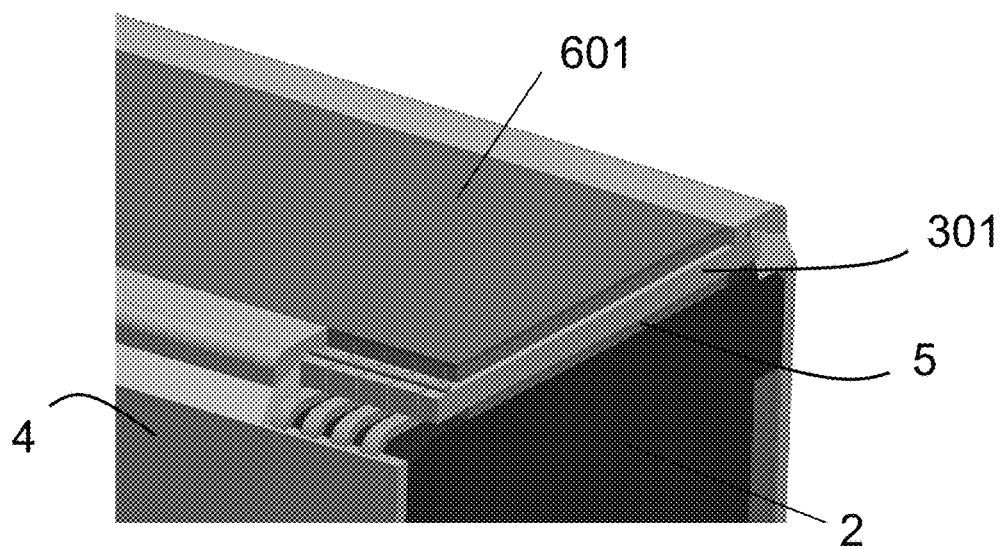
FIG. 6 schematically shows a probe head according to another embodiment.

Thus the idea of using a reflecting interface 5 between backing 2 and electrode 101 as shown in FIGS. 4 to 6 to allow more energy to be directed towards the front face resulting in a stronger pulse, thus enhanced sensitivity, and reduced heating.

A small thickness (generally ¼ of the incident wave wavelength) back-matching layer 5 interposed between backing 2 and electrode 101 modifies the bulk effective acoustic impedance as follows $$Z_{eff} = (Z_{layer})^2 / Z_{backing}$$

As the backing acoustical properties are substantially modified, the back-matching layer has to be carefully chosen.

The prior art has mainly focused in implementing high Z de-matching layers (see for example U.S. Pat. No. 7,621,028). This choice has some advantages, as a short pulse length and smaller ringing, but some drawbacks, for example for medium range frequencies (starting from 5-6 MHz) the bonding quality between piezoelectric metallization 101 and de-matching layer becomes critical. Furthermore, the quarter-wavelength resonance for piezo implies the use of small thickness piezoelectric material, more difficult to handle and manufacture for high frequency probes.

The inventors followed an opposite approach. i.e. studied the behaviour of back-matching layers having small impedance with half-wavelength resonance for piezo.

As some of such materials have themselves good adhesive properties, embodiments herein relate to the use of a back-matching layer also in the form of an adhesive layer for the creation of the subassembly piezo/backing with a reduced number of manufacturing steps.

The following table shows the characteristics of the studied material in terms of impedance of the back-matching layer (Z), impedance of the subassembly back-matching/backing (Zeff) and reflection at the piezo interface (Reflection %). The impedance of the backing material is typically higher than the acoustic impedance of the back-matching layer. In the example shown in the table, it is approximately 7 MRayl.

|  | Z (MRayls) | Zeff (MRayls) | Reflection % |
| --- | --- | --- | --- |
| Epoxy | 3 | 1.3 | 70% |
| Epoxy + microspheres | 2 | 0.56 | 85% |
| Epoxy + thermo-expandable particles | 1.8-0.5 | 0.46-0.04 | 88%-99% |

Figure 7:
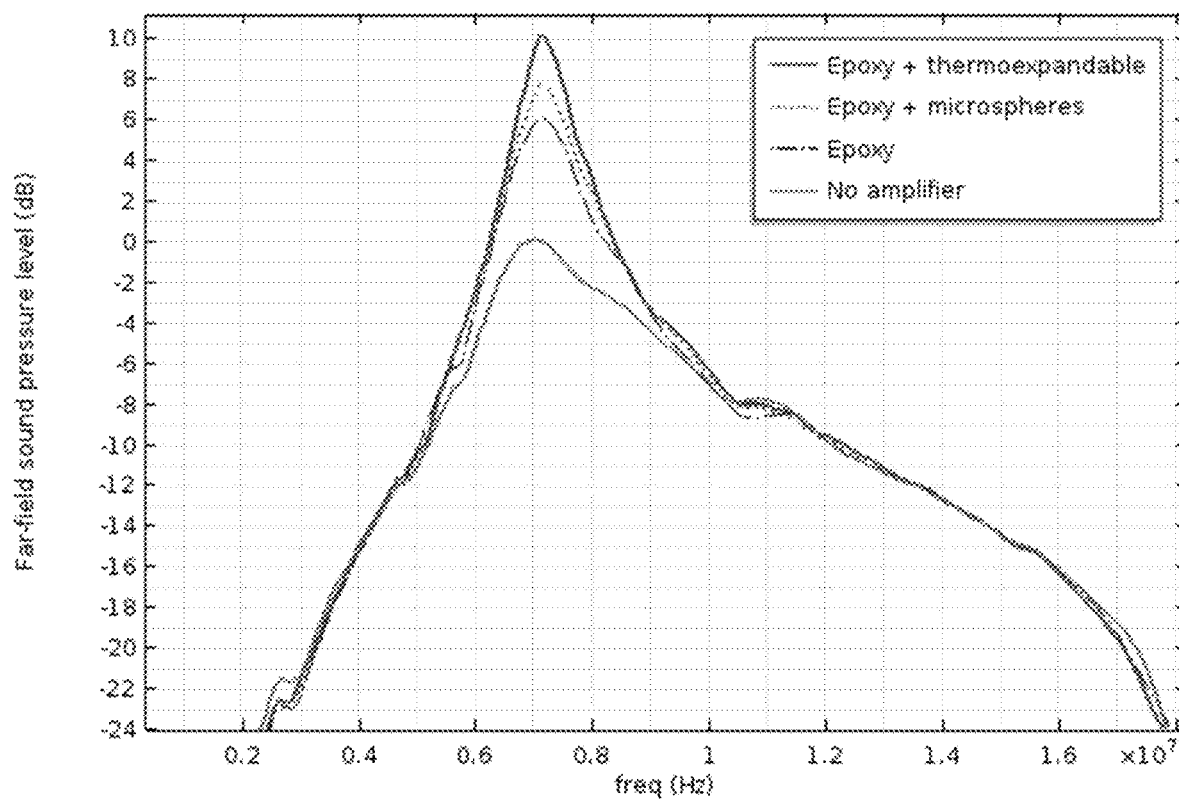
FIG. 7 shows the sensitivity comparison for various back-matching layer materials, without front matching layers.

As it can be appreciated by looking at FIG. 7 showing the sensitivity comparison for various back-matching layer materials, it is possible to achieve high degree of sensitivity particularly if the impedance is kept very low.

As an example, a reduced Z material has been obtained by embedding in an epoxy matrix low density particles, like hollow glass microspheres or thermo-expandable particles such as, for example, microcapsules encapsulating liquid low-boiling-point hydrocarbon in shells of thermoplastic resin like $VCl_2$-AN copolymer (chlorine containing shell), AN copolymer (chlorine-free shell). When the microcapsules added to the polymer, for example epoxy, are heated, the shells are softened and expanded with the pressure of gasified hydrocarbon while the polymer cures. A microcapsule expand into 50 to 100 times of its original volume (ballooning) and the cured polymer, where the heated microcapsules are dispersed, can have bulk density as small as 0.4 g/cm3 and acoustic impedance of 0.7-0.8 MRayl. By adjusting microcapsules concentration (% volume) in polymer and curing, the density/acoustic impedance of the material forming the back-matching layer can be fine-tuned.

For glass microspheres the particle size is determined by the manufacturer, while for thermo-expandable particles an optimization is possible by acting both on concentration (number of particles per unit volume) and curing heating process (final particle size). In our analysis a range of 0.5-1.8 MRayl impedance has been considered. In FIG. 6 the curve labelled as Epoxy+thermo-expandable particles is related to the 0.8 MRayl acoustic impedance. Other results are intermediate between this and the Epoxy+microspheres curve (whose impedance is similar to the 1.8 max impedance considered in the thermo-expandable specimens).

Optimal back-matching layer thicknesses typically range from 1/3.5 to ⅛ of the central wavelength. Gains are between +6 and +10 dB.

Figure 8:
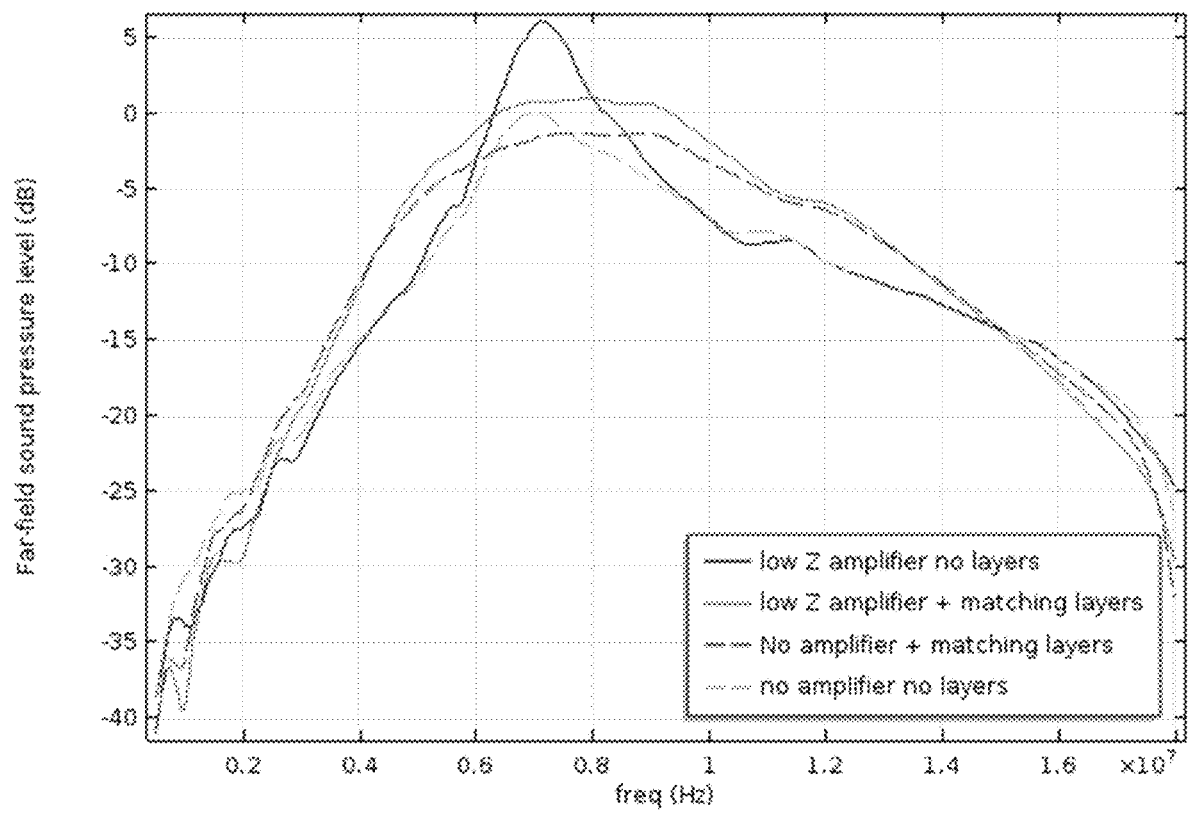
FIG. 8 shows the effect on band of two optimized front matching layers with pure epoxy back-matching layer as low Z amplifier. Comparison is made with the standard structure (the same front matching layers without any back-matching layer).

FIG. 8 shows the effect on band of two optimized front matching layers with an epoxy back-matching layer as low Z amplifier. Comparison is made with the standard structure (the same front matching layers without any back-matching layer). The front matching layers are made of epoxy loaded with Tungsten particles in order to obtain intermediate acoustic impedances (about 8 MRayl and 3 MRayl, respectively). In this case, the back-matching layer is pure epoxy. The band obtained with the back-matching layer and front matching layers is typically in the range of 65-78%.

As it can be appreciated by looking at the figure, the presence of front matching layers has the effect of redistributing the energy to a wider spectrum of frequencies, resulting in a lower peak (i.e. lower sensitivity) either with the back-matching layer (indicated as low Z amplifier in the legend) or without any back-matching layer. Nevertheless, the curve with amplifier plus front matching layers remains always above the correspondent curve with no amplifier plus matching layers, indicating that there is a net energy gain. The sensitivity raise is +3 dB in this case.

Figure 9:
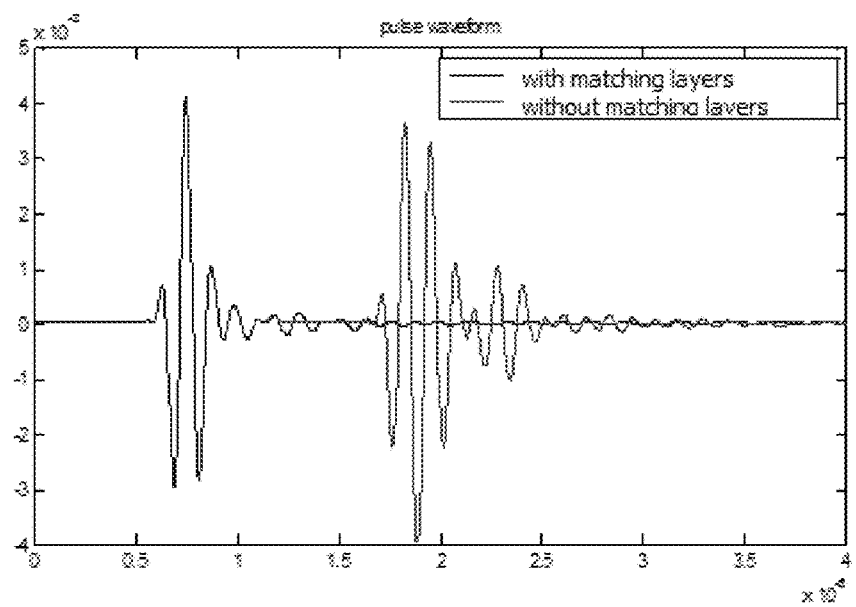
FIG. 9 shows an example of the pulse length reduction with two selected front matching layers.

The resulting pulse is considerably shorter after the front layers application, as shown in FIG. 9. The −20 dB pulse length is reduced from 0.750 μs to 0.295 μs.

Figure 10:
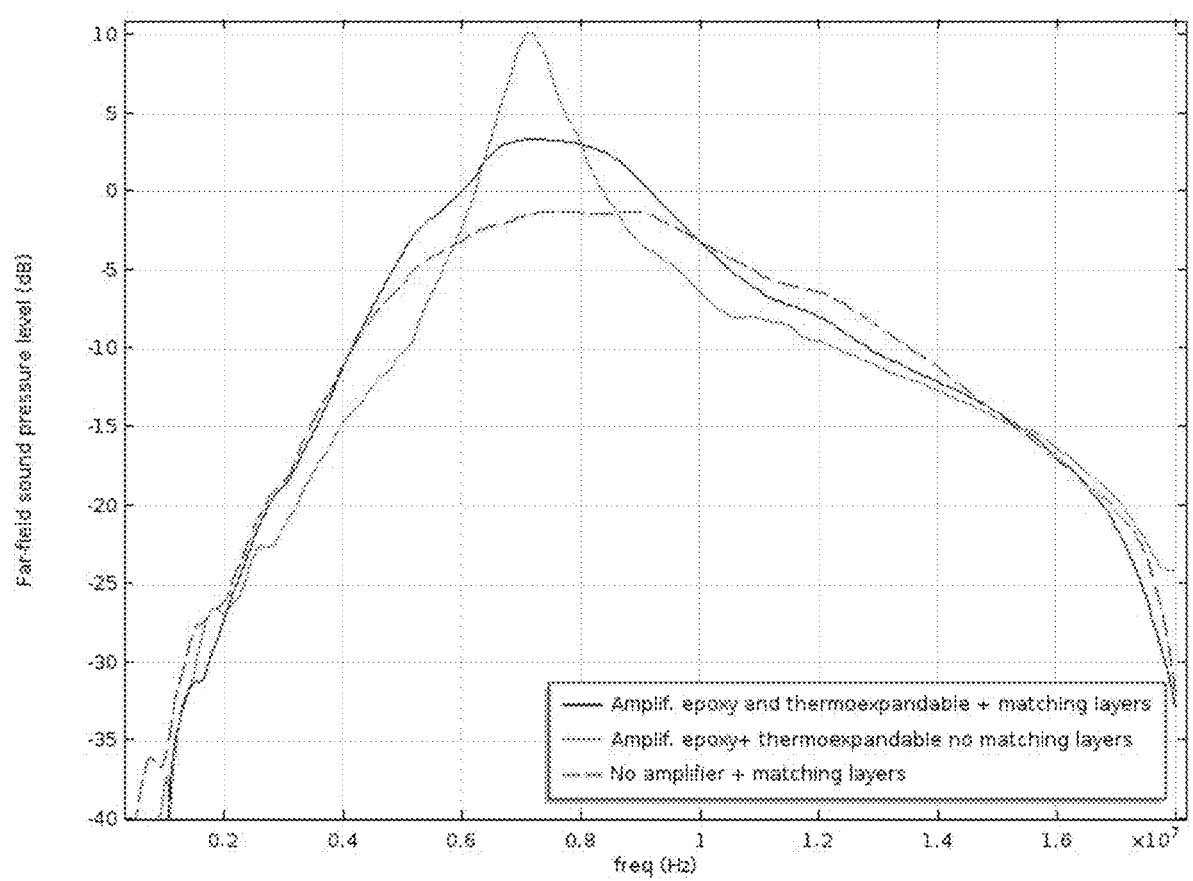
FIG. 10 shows the effect on band of two other optimized front matching layers when the back-matching layer is made of epoxy+thermoexpandable particles cured at 110° C. In comparison with FIG. 8 a higher sensitivity is gained.

As a further example, FIG. 10 shows the effect of front matching layers application over an acoustic stack with back-matching layer made of epoxy and thermo-expandable particles with acoustic impedance of 0.8 MRayls.

Figure 11:
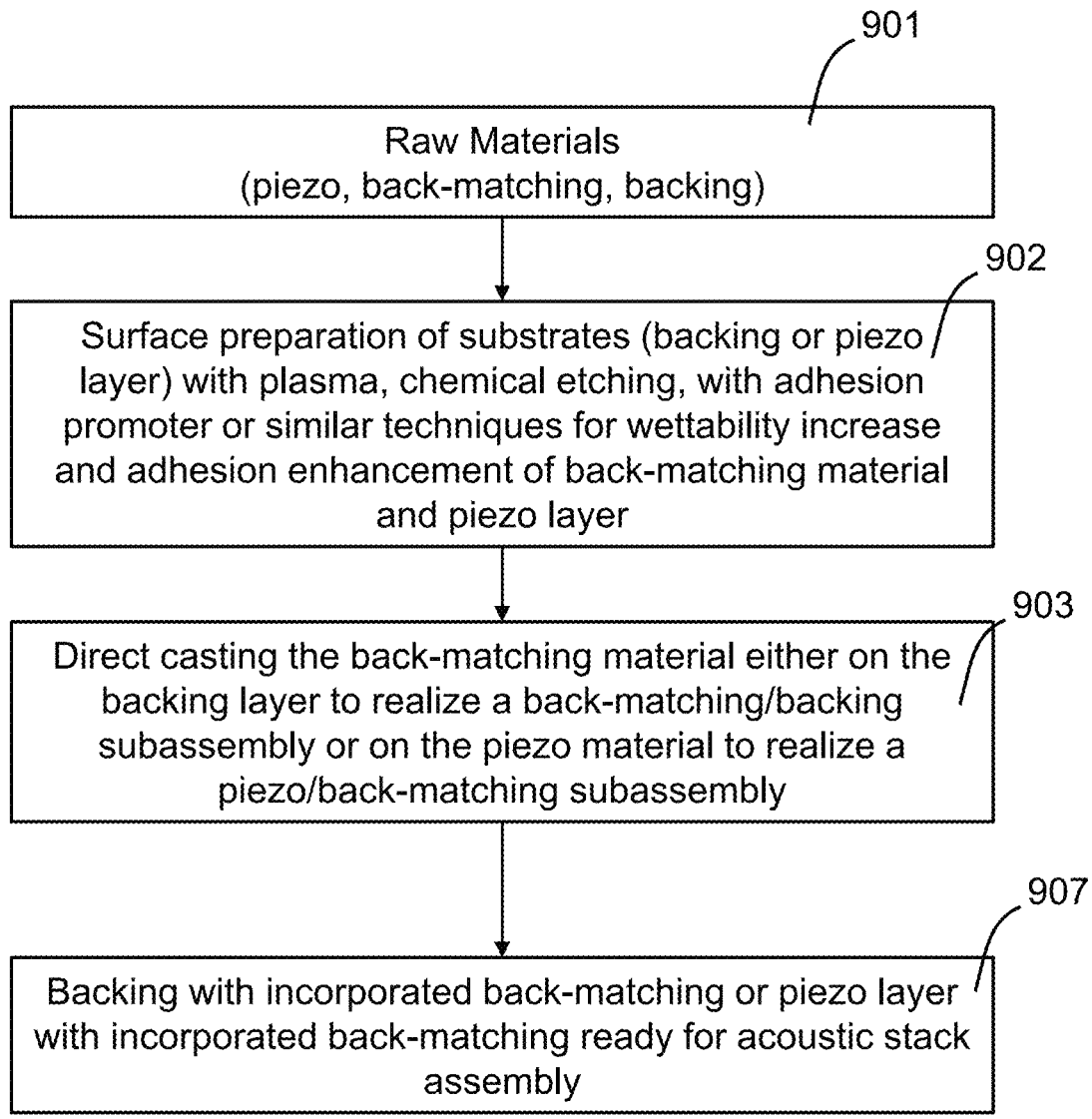
FIG. 11-14 are flowcharts of process for manufacturing a transducer assembly according to embodiments herein.

FIG. 11 shows a flowchart of a process for manufacturing a transducer assembly according to embodiments herein, wherein a polymer, such as epoxy, is used for the back-matching layer.

At 901, Raw Materials (piezo, back-matching, backing) are provided.

At 902 the surface of the substrates (backing and/or piezo layer) are prepared, for example with plasma, chemical etching, with adhesion promoter or similar techniques for wettability increase and adhesion enhancement of back-matching material or piezo layer.

At 903 the back-matching material is casted either on the backing layer to realize a back-matching/backing subassembly or on the piezo material to realize a piezo/back-matching subassembly. In case of casting on piezo, bottom electrical connections are realized before casting.

At 907 backing with incorporated back-matching or piezo layer with incorporated back-matching is ready for acoustic stack assembly.

Figure 12:
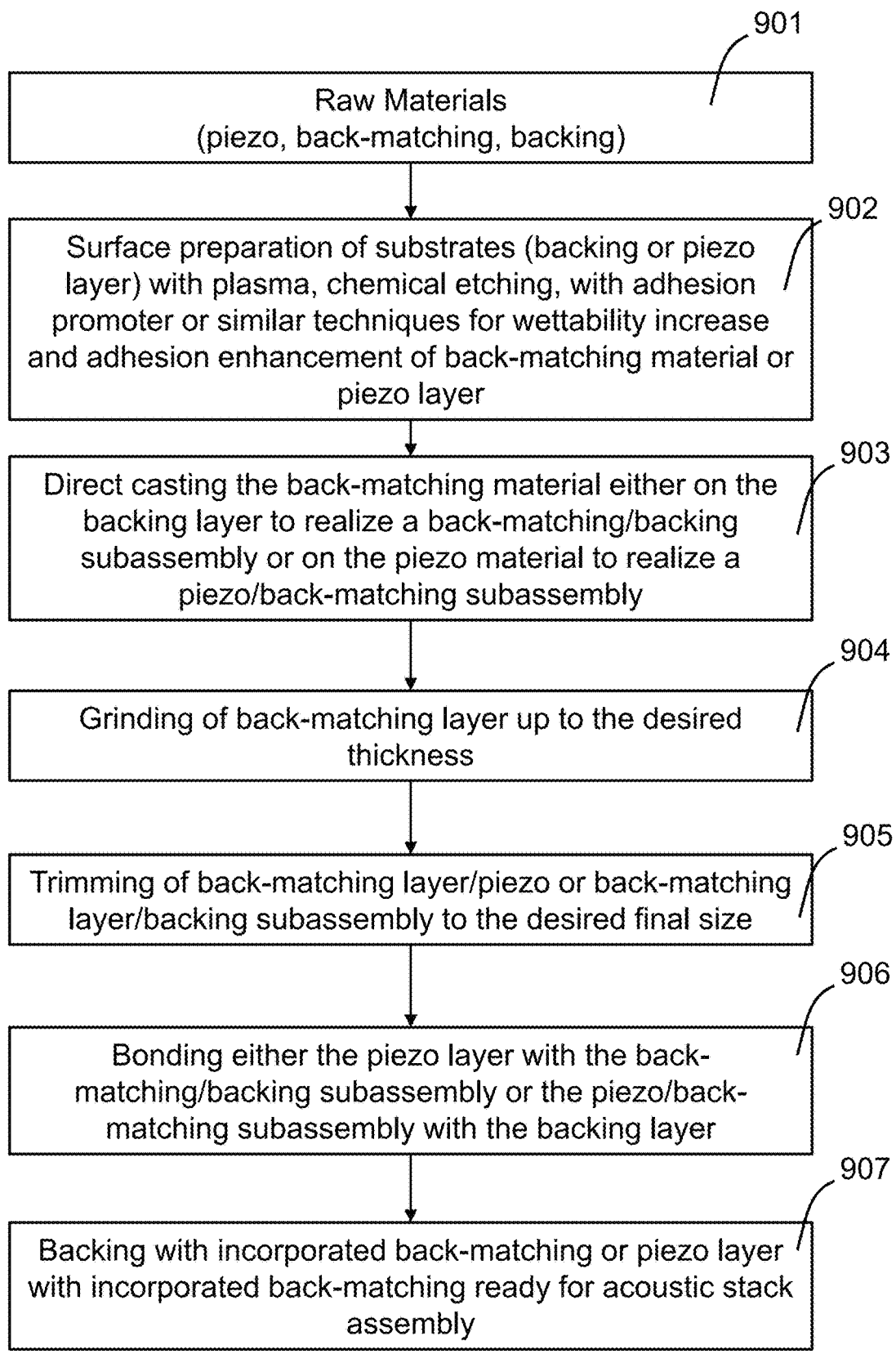

As shown in FIG. 12, further operations may include:

At 904 grinding of back-matching layer up to the desired thickness (905);

At 905 trimming of back-matching layer/piezo or back-matching layer/backing subassembly to the desired final size (906);

At 906 bonding either the piezo layer with the back-matching/backing subassembly or the piezo/back-matching subassembly with the backing layer (906).

Figure 13:
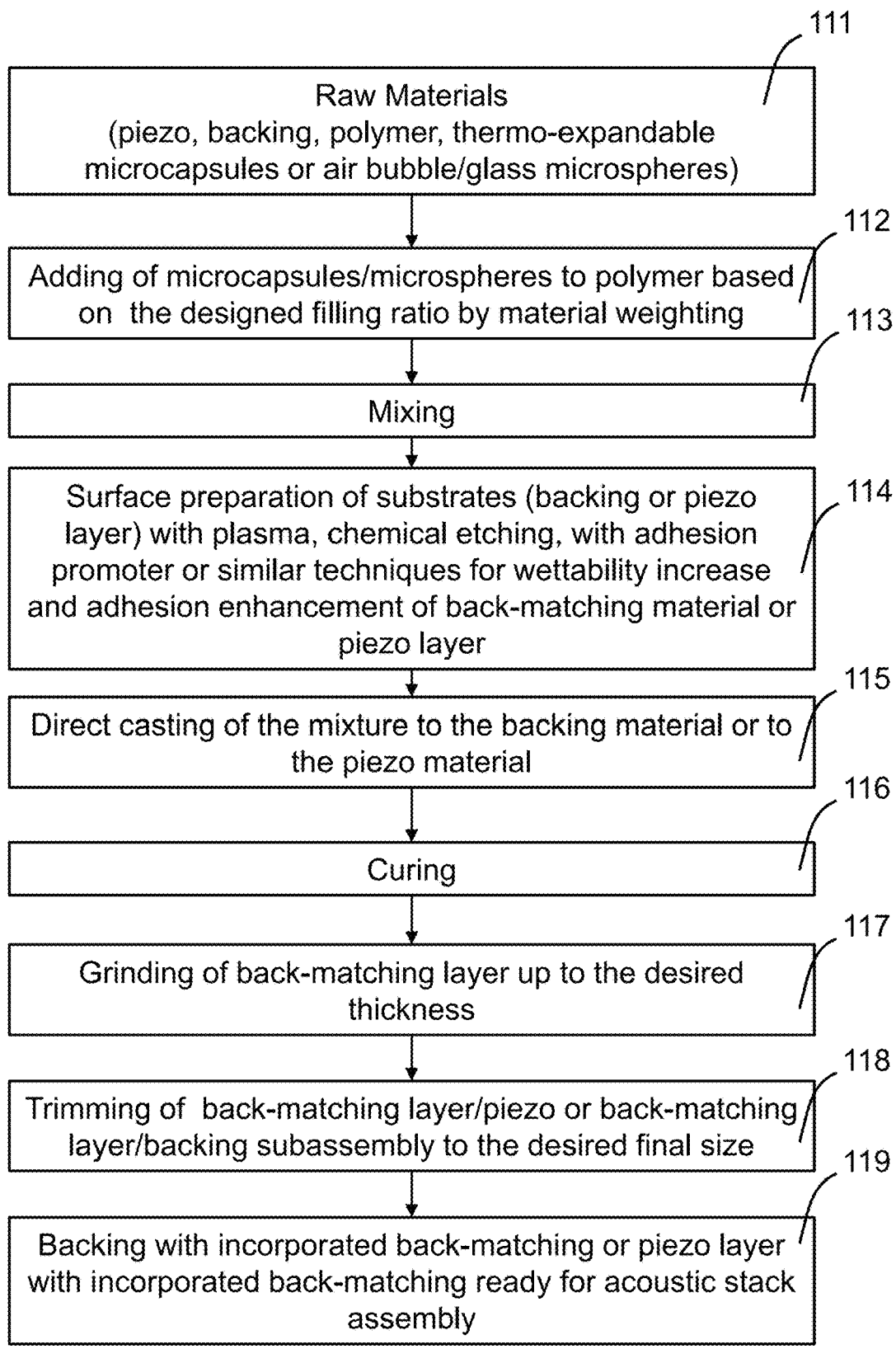

FIG. 13 shows a flowchart of a process for manufacturing a transducer assembly according to another embodiment wherein thermo-expandable microcapsules or air bubble/glass microspheres are used for the back-matching layer.

At 111 Raw Materials (piezo, backing, polymer, thermo-expandable microcapsules or air bubble/glass microspheres) are provided.

At 112 the microcapsules/microspheres are added to the polymer based on the designed filling ratio by material weighting.

At 113 polymer and microcapsules are mixed, for example, with speedmixer in order to avoid air entrapment.

At 114 the surface of the substrates (backing and/or piezo layer) are prepared, for example with plasma, chemical etching, with adhesion promoter or similar techniques for wettability increase and adhesion enhancement of back-matching material or piezo layer.

At 115 the mixture is casted to the backing material or to the piezo material. In case of casting on piezo, bottom electrical connections are realized before casting. Vacuum degassing can be advantageously adopted.

At 116 a curing step is provided to allow thermal expansion of the microcapsules.

At 117 the back-matching layer is grinded up to the desired thickness.

At 118 back-matching layer/piezo or back-matching layer/backing subassembly is trimmed to the desired final size.

At 119 backing with incorporated back-matching or piezo layer with incorporated back-matching is ready for acoustic stack assembly.

Figure 14:
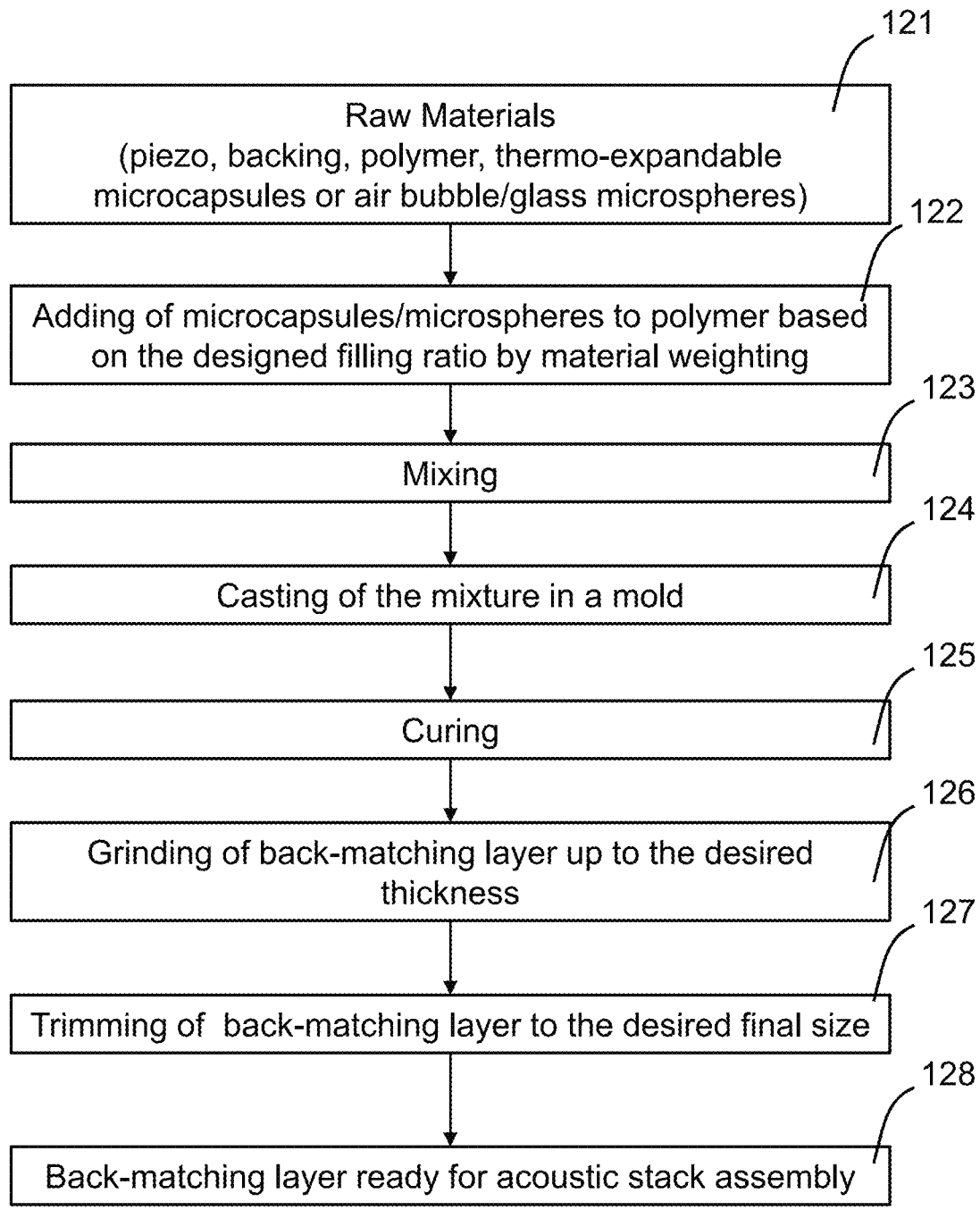

Alternatively, the back-matching layer can be produced as a standalone component and then bonded to the piezo layer or the backing. To such extent in the embodiment disclosed in FIG. 14:

At 121 Raw Materials (piezo, backing, polymer, thermo-expandable microcapsules) are provided.

At 122 the microcapsules are added to the polymer based on the designed filling ratio by material weighting.

At 123 polymer and microcapsules are mixed, for example, with speedmixer in order to avoid air entrapment.

At 124 the so obtained mixture is cast in a mold. Vacuum degassing can be advantageously adopted.

At 125 a curing step is provided to allow thermal expansion of the microcapsules.

At 126 the back-matching layer is grinded up to the desired thickness.

At 127 the back-matching layer is trimmed to the desired final size.

At 128 the back-matching layer ready for bonding with adhesives to realize an acoustic stack assembly.

All the process steps can be performed in any meaningful order and are not all necessary. For example grinding and trimming steps are obviously optional in all the embodiments herein disclosed as well as the surface preparation that can certainly be omitted. A variant could be to use adhesive properties of the back-matching layer to allow a direct bonding to piezo and/or backing. All without departing from the guiding principle of the invention disclosed above and claimed below.

The invention claimed is:

1. A transducer assembly operable to transmit ultrasonic energy in a desired direction towards a zone adapted to be acoustically coupled to an object or area of interest, the transducer assembly comprising:
    a) a transducer layer;
    b) a backing layer disposed behind the transducer layer with respect to the desired direction;
    c) a back-matching layer disposed between the transducer layer and the backing layer to reflect towards the transducer layer part of the ultrasonic energy directed from the transducer layer to the backing layer,
wherein the backing layer has an acoustic impedance higher than an acoustic impedance of the back-matching layer, the back-matching layer has an acoustic impedance less than an acoustic impedance of the transducer layer and the transducer layer has a thickness greater than a ¼ of a wavelength of ultrasound waves the transducer assembly is configured to generate.

2. The transducer assembly according to claim 1, wherein the transducer layer has a thickness that is half of the wavelength.

3. The transducer assembly according to claim 1, wherein the transducer assembly comprises one or more front acoustic matching layers arranged as a stack starting from the transducer layer towards the zone, the one or more front acoustic matching layers having a thickness less than half of the wavelength, particularly not greater than ⅓ of the wavelength, and being configured to compensate for increase in pulse duration of an ultrasound wave directed towards the desired direction caused by the acoustic impedance of the back-matching layer.

4. The transducer assembly according to claim 1, wherein the back-matching layer has an impedance less than 5 MRayl, particularly between 0.5 and 4 MRayl, typically between 0.6-2 MRayl, more typically between 0.7 and 1 MRayl.

5. The transducer assembly according to claim 1, wherein the back-matching layer comprises or is formed by a material having adhesive properties.

6. The transducer assembly according to claim 1, wherein the back-matching layer comprises a polymer such as epoxy, powder/particle filled epoxy, polyurethanes, or acrylics.

7. The transducer assembly according to claim 1, wherein the back-matching layer comprises air bubble-glass microspheres or thermic expandable particles to control a density of a material forming the back-matching layer.

8. The transducer assembly according to claim 1, wherein the back-matching layer and the backing layer form a subassembly having impedance between 0.04 and 1.3 MRayl.

9. A transducer assembly operable to transmit ultrasonic energy in a desired direction towards a zone adapted to be acoustically coupled to an object or area of interest, the transducer assembly comprising:
   a) a transducer layer having a having a thickness greater than a ¼ of the wavelength of the ultrasound waves the transducer assembly is configured to generate;
   b) a backing layer disposed behind the transducer layer with respect to the desired direction;
   c) a back-matching layer disposed between the transducer layer and the backing layer to reflect towards the transducer layer part of the ultrasonic energy directed from the transducer layer to the backing layer,
wherein the back-matching layer has an impedance less than thean impedance of the transducer layer and comprises air bubble-glass microspheres or thermic expandable particles to control a density of a material forming the back-matching layer.

10. The transducer assembly according to claim 9, wherein the thermic expandable particles comprise bubbles encapsulating liquid hydrocarbon in shells of thermoplastic resin like $VCl_2$-AN copolymer or AN copolymer.

11. The transducer assembly according to claim 9, wherein the back-matching layer and the backing layer form a subassembly having impedance between 0.04 and 1.3 MRayl.

12. A process for manufacturing a transducer assembly operable to transmit ultrasonic energy in a desired direction towards a zone adapted to be acoustically coupled to an object or area of interest, the process comprising:
   providing a transducer layer having a thickness greater than a ¼ of the wavelength of the ultrasound waves the transducer assembly is configured to generate;
   providing a backing layer;
   providing a back-matching material having an acoustic impedance less than an acoustic impedance of the transducer layer;
   direct casting the back-matching material either on the backing layer to realize a back-matching material and backing layer subassembly or on the transducer layer to realize a transducer layer and back-matching material subassembly;
   bonding either the transducer layer with the back-matching material and backing layer subassembly or the transducer layer and back-matching material subassembly with the backing layer.

13. The process according to claim 12, further comprising:
   preparing a surface of the transducer layer or of the backing layer for wettability increase and adhesion enhancement of the back-matching material or the transducer layer;
   grinding of the back-matching material to a pre-determined thickness.

14. The process according to claim 12, wherein the back-matching material comprises one or more polymers, particularly epoxies, polyurethanes, or acrylics.

15. The process according to claim 12, further comprising:
   providing air bubble-glass microspheres or thermo-expandable microcapsules;
   adding the air bubble-glass microspheres or the thermic expandable particles to the back-matching material; and
   mixing the back-matching material with the microspheres/ microcapsules.

16. The process according to claim 12, the providing a transducer layer step further comprises providing a transducer layer having a thickness of ½ of the wavelength of the ultrasound waves the transducer assembly is configured to generate.

17. The process according to claim 12, wherein the back-matching material and backing layer subassembly has impedance between 0.04 and 1.3 MRayl.

18. A process for manufacturing a transducer assembly operable to transmit ultrasonic energy in a desired direction towards a zone adapted to be acoustically coupled to an object or area of interest, the process comprising:
   providing a transducer layer having a thickness greater than a ¼ of the wavelength of the ultrasound waves the transducer assembly is configured to generate;
   providing a backing layer;
   providing a back-matching material having an acoustic impedance less than an acoustic impedance of the transducer layer;
   providing air bubble-glass microspheres or thermo-expandable microcapsules;
   adding the air bubble-glass microspheres or the thermo-expandable microcapsules to the back-matching material;
   mixing the back-matching material with the air bubble-glass microspheres or the thermo-expandable microcapsules;
   direct casting the back-matching material either on the backing layer to realize a back-matching material and backing layer subassembly or on the transducer layer to realize a transducer layer and back-matching material subassembly;
   bonding either the transducer layer with the back-matching material and backing layer subassembly or the transducer layer and back-matching material subassembly with the backing layer.

19. The process according to claim 18, further comprising curing the back-matching material or the back-matching material and backing layer subassembly or the transducer layer and back-matching material subassembly to control the acoustic impedance of the back-matching material.

20. The process according to claim 18, wherein the thermo-expandable microcapsules encapsulate liquid low-boiling-point hydrocarbon in shells of thermoplastic resin like $VCl_2$-AN copolymer or AN copolymer.

21. The process according to claim 18, wherein curing is performed at a temperature that allows the thermo-expandable microcapsules to expand from 50 to 100 times their original volume to bring thea density of the back-matching material less than 0.6 g/cm3, typically in the range 0.3-0.5 g/cm3, more typically equal or less than 0.4 g/cm3 and thus the acoustic impedance of the back-matching material less than 1 MRayl, typically between 0.6-0.9 MRayl, more typically between 0.7-0.9 MRayl.

22. The process according to claim 18, wherein the back-matching material and backing layer subassembly has impedance between 0.04 and 1.3 MRayl.

* * * * *